US011311388B2

(12) United States Patent
Frock et al.

(10) Patent No.: US 11,311,388 B2
(45) Date of Patent: Apr. 26, 2022

(54) INTERSPINOUS PROCESS IMPLANT

(71) Applicant: Spinal Simplicity, LLC, Overland Park, KS (US)

(72) Inventors: Melissa Frock, Larwill, IN (US); Adam Frock, Larwill, IN (US); Todd Moseley, Olathe, KS (US); Adam Rogers, Overland Park, KS (US)

(73) Assignee: Spinal Simplicity, LLC, Overland Park, KS (US)

( * ) Notice: Subject to any disclaimer, the term of this patent is extended or adjusted under 35 U.S.C. 154(b) by 0 days.

(21) Appl. No.: 16/998,171

(22) Filed: Aug. 20, 2020

(65) Prior Publication Data
US 2022/0054279 A1 Feb. 24, 2022

(51) Int. Cl.
*A61F 2/44* (2006.01)
*A61B 17/70* (2006.01)
*A61F 2/30* (2006.01)

(52) U.S. Cl.
CPC ........ *A61F 2/4455* (2013.01); *A61B 17/7062* (2013.01); *A61F 2002/30062* (2013.01); *A61F 2002/30957* (2013.01); *A61F 2002/30985* (2013.01); *A61F 2310/00023* (2013.01); *A61F 2310/00796* (2013.01)

(58) Field of Classification Search
CPC .............. A61F 2/4405; A61B 17/7062; A61B 17/7065; A61B 17/7067; A61B 17/7068
USPC .................................................. 606/248, 249
See application file for complete search history.

(56) References Cited

U.S. PATENT DOCUMENTS

| | | | |
|---|---|---|---|
| 4,573,844 A | 3/1986 | Smith | |
| 5,098,433 A | 3/1992 | Freedland | |
| 7,070,598 B2* | 7/2006 | Lim | A61B 17/025 606/99 |
| 7,226,261 B1 | 6/2007 | Bristol | |
| 8,343,190 B1 | 1/2013 | Mueller et al. | |
| 8,628,577 B1* | 1/2014 | Jimenez | A61F 2/4611 623/17.15 |
| 8,672,976 B2* | 3/2014 | Kilpela | A61B 17/7071 606/249 |
| 9,119,726 B2* | 9/2015 | Wei | A61F 2/442 |
| 9,668,879 B2* | 6/2017 | Jimenez | A61F 2/447 |
| 10,137,006 B2* | 11/2018 | Dewey | A61F 2/4611 |
| 10,779,955 B2* | 9/2020 | Kuyler | A61F 2/447 |
| 2004/0193158 A1* | 9/2004 | Lim | A61B 17/025 606/99 |
| 2004/0208722 A1 | 10/2004 | Kuenzel | |
| 2005/0129482 A1 | 6/2005 | Wang | |

(Continued)

OTHER PUBLICATIONS

PCT Application No. PCT/US2021/044609 International Search Report and Written Opinion, dated Dec. 21, 2021.

*Primary Examiner* — Nicholas J Plionis
(74) *Attorney, Agent, or Firm* — Erise IP, P.A.

(57) ABSTRACT

A system and method for providing a spinal implant having a main body, a proximal anchor, a distal anchor, and an internal plunger. The proximal anchor comprises a nut having an internal bore. The distal anchor comprises a plurality of wings having a first closed configuration and a second open configuration. The internal plunger is housed within a central bore of the main body. The distal end of the internal plunger is operatively connected to the first wing and the second wing to selectively move the wings between the first closed configuration and the second open configuration, and vice versa.

20 Claims, 13 Drawing Sheets

(56) References Cited

U.S. PATENT DOCUMENTS

| | | | |
|---|---|---|---|
| 2005/0182416 A1* | 8/2005 | Lim | A61B 17/025 |
| | | | 606/90 |
| 2006/0085070 A1 | 4/2006 | Kim | |
| 2006/0264938 A1* | 11/2006 | Zucherman | A61B 17/7068 |
| | | | 606/249 |
| 2008/0021468 A1* | 1/2008 | Zucherman | A61B 17/7068 |
| | | | 606/249 |
| 2008/0108990 A1* | 5/2008 | Mitchell | A61B 17/7065 |
| | | | 606/305 |
| 2008/0114367 A1* | 5/2008 | Meyer | A61F 2/441 |
| | | | 606/90 |
| 2008/0147190 A1 | 6/2008 | Dewey et al. | |
| 2008/0177391 A1* | 7/2008 | Mitchell | A61B 17/7068 |
| | | | 623/17.16 |
| 2008/0183211 A1 | 7/2008 | Lamborne et al. | |
| 2008/0243250 A1 | 10/2008 | Seifert et al. | |
| 2010/0057130 A1 | 3/2010 | Yue | |
| 2010/0152775 A1 | 6/2010 | Seifert et al. | |
| 2010/0234889 A1* | 9/2010 | Hess | A61B 17/7068 |
| | | | 606/249 |
| 2014/0194930 A1* | 7/2014 | Hess | A61B 17/7065 |
| | | | 606/249 |
| 2015/0112387 A1* | 4/2015 | Hess | A61B 17/00234 |
| | | | 606/249 |
| 2016/0166396 A1* | 6/2016 | McClintock | A61F 2/4425 |
| | | | 623/17.16 |
| 2016/0262805 A1* | 9/2016 | Rogers | A61B 17/7065 |
| 2017/0296238 A1* | 10/2017 | Snell | A61F 2/4611 |

\* cited by examiner

INTERSPINOUS PROCESS IMPLANT

BACKGROUND

1. Field

Embodiments of the invention relate to spinal implants. More specifically, embodiments of the invention relate to a percutaneously or posteriorly introduced spinous process implant and fusion device.

2. Related Art

The spine consists of a column of twenty-four vertebrae that extend from the skull to the hips. Discs of soft tissue are disposed between adjacent vertebrae. In addition, the spine encloses and protects the spinal cord, defining a bony channel around the spinal cord, called the spinal canal. There is normally a space between the spinal cord and the borders of the spinal canal so that the spinal cord and the nerves associated therewith are not pinched.

Over time, the ligaments and bone that surround the spinal canal can thicken and harden, resulting in a narrowing of the spinal canal and compression of the spinal cord or nerve roots. This condition is called spinal stenosis, which results in pain and numbness in the back and legs, weakness and/or a loss of balance. These symptoms often increase after walking or standing for a period of time.

There are a number of non-surgical treatments for spinal stenosis. These include non-steroidal anti-inflammatory drugs to reduce the swelling and pain, and corticosteroid injections to reduce swelling and treat acute pain. While some patients may experience relief from symptoms of spinal stenosis with such treatments, many do not, and thus turn to surgical treatment. The most common surgical procedure for treating spinal stenosis is decompressive laminectomy, which involves removal of parts of the vertebrae. The goal of the procedure is to relieve pressure on the spinal cord and nerves by increasing the area of the spinal canal.

Interspinous process decompression (IPD) is a less invasive surgical procedure for treating spinal stenosis. With IPD surgery, there is no removal of bone or soft tissue. Instead, an implant or spacer device is positioned behind the spinal cord or nerves and between the interspinous processes that protrude from the vertebrae in the lower back.

Examples of a particularly useful interspinous process implant and fusion devices are disclosed in commonly assigned U.S. Pat. Nos. 9,861,399, 8,945,184; 9,314,276, 9,907,581, and 9,757,164, the disclosures of which are all incorporated herein by reference in their entirety.

The invention provides an improvement over prior interspinous implant devices by constructing an implant that is substantially shorter in length than prior devices. This will advantageously reduce the overall size and profile of the device, thereby making implantation safer and easier.

The construction of the implant according to an embodiment of the invention also allows for easier removal of the device after implantation, if desired. The ability of the surgeon to both selectively open and close the wings of the device is another advantage over prior devices. Because the wings can be closed after implantation, the implant of the invention can be removed by the same small lateral incision through which it was originally inserted. Removal of prior devices generally requires an additional posterior incision to manually close the wings before the device can be extracted.

Additionally, the device of the invention does not require a removable end piece. This improves the safety and ease of the procedure by reducing the number of steps in the implantation process. Fewer separable parts of the implant also reduces cost and simplifies manufacturing.

SUMMARY

Embodiments of the invention solve the above-mentioned problems by providing a system and method for minimally invasive spinal fusion.

A first embodiment of the invention is directed to a spinal implant comprising: a main body, a proximal anchor, a distal anchor, and an internal plunger. The main body has an outer surface, a central bore therein, a proximal end, a distal end, and a longitudinal axis extending therebetween. The proximal anchor comprises a nut having a proximal side, a distal side, and an internal bore. The distal anchor comprises a plurality of wings having a first closed configuration and a second open configuration, wherein the plurality of wings comprises a first wing and a second wing. The internal plunger has a proximal end, a distal end, and is housed within the central bore of the main body. The distal end of the internal plunger is operatively connected to the first wing and the second wing to selectively move the plurality of wings between the first closed configuration and the second open configuration.

A further embodiment of the invention is directed to a spinal implant comprising a main body, a proximal anchor, a distal anchor, and a linkage assembly. The main body has an outer surface, a central bore therein, a proximal end, a distal end, and a longitudinal axis extending therebetween. The main body includes external threads on at a least a portion of the outer surface. The proximal anchor comprises a nut having a proximal side, a distal side, and an internal bore having internal threads. The distal anchor comprises a first wing and a second wing configured to be selectively opened and closed. The linkage assembly connects the first wing and the second wing to the main body.

Another embodiment of the invention is directed to a method of placing a spinal implant at a treatment site comprising: providing a spinal implant in a first closed configuration; placing the spinal implant in a patient at a desired treatment site; and sliding the internal plunger distally along the longitudinal axis to move the plurality of wings to the second open configuration. The method may further comprise sliding the internal plunger proximally along the longitudinal axis to move the plurality of wings to the first closed configuration to withdraw the spinal implant from the patient.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the invention will be apparent from the following detailed description of the embodiments and the accompanying drawing figures.

BRIEF DESCRIPTION OF THE DRAWING FIGURES

Embodiments of the invention are described in detail below with reference to the attached drawing figures, wherein.

Figure 1:
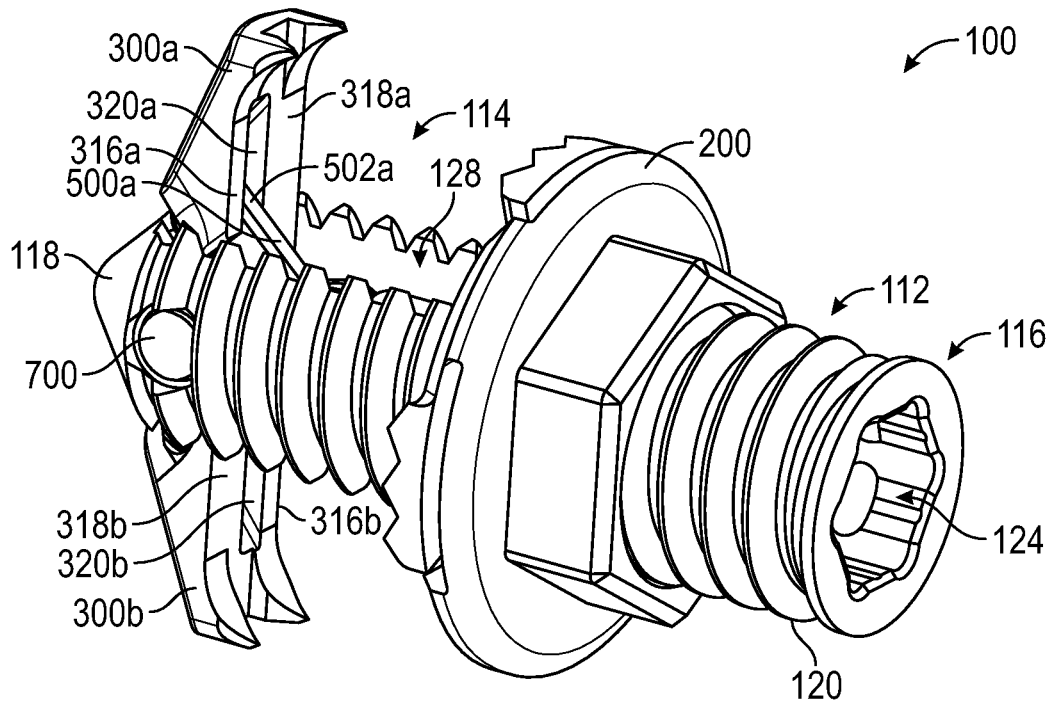
FIG. 1 is a perspective view of a first embodiment of the implant of the invention in an open configuration.

The drawing figures do not limit the invention to the specific embodiments disclosed and described herein. The drawings are not necessarily to scale, emphasis instead being placed upon clearly illustrating the principles of the invention.

DETAILED DESCRIPTION

The following detailed description references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the invention. The following detailed description is, therefore, not to be taken in a limiting sense. The scope of the invention is defined only by the appended claims, along with the full scope of equivalents to which such claims are entitled.

In this description, references to "one embodiment," "an embodiment," or "embodiments" mean that the feature or features being referred to are included in at least one embodiment of the technology. Separate references to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the technology can include a variety of combinations and/or integrations of the embodiments described herein.

Embodiments of the invention are directed to a minimally invasive interspinous-interlaminar fusion device for the temporary fixation of the thoracic, lumbar, and sacral spine while waiting for bony fusion to occur. The implant can be attached to the posterior non-cervical spine at the spinous processes to provide immobilization and stabilization of the spinal segments. A threaded main body of the implant provides controlled distraction.

One embodiment of the invention is shown in FIG. 1, which illustrates an interspinous process implant 100 in an open configuration. Implant 100 may include a main body 112 having a distal end 114 and a proximal end 116. Implant 100 further includes a nut 200 on the proximal end 116 of main body 112 and extendable first and second wings 300a, 300b on the distal end 114 of main body 112. As can be seen in the cross-sectional view of FIG. 2, implant 100 further includes a plunger 400 and first and second linkages 500a, 500b for operatively connecting first and second wings 300a, 300b to main body 112, as will be described herein.

Figure 3:
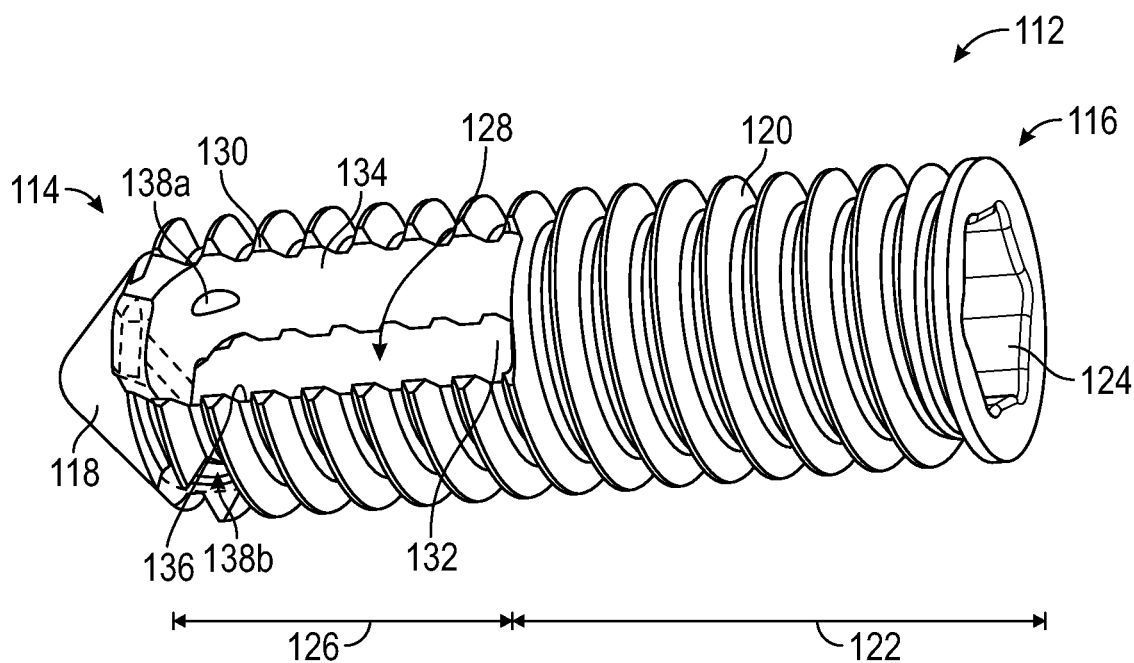
FIG. 3 is a perspective view of an embodiment of the main body of the invention.

FIG. 3 illustrates an embodiment of main body 112. Distal end 114 includes a conical distal tip 118 having a rounded distalmost end. In some embodiments, the conical distal tip has a sharp pointed distalmost end. In some embodiments, main body 112 includes helical threads 120 on an exterior surface thereof. In some embodiments, main body 112 may alternatively or additionally include cutting threads or box threads. Helical threads 120 may be provided along the entire exterior surface of main body 112 or along only a portion of the exterior surface of main body 112. In some embodiments, the threads may have a depth of about 0.5 to about 3.0 mm, an angle of about 45° to about 100°, and a spacing of about 1.0 mm to about 4.0 mm. In some embodiment, the threads may have a depth of about 1.0 mm, an angle of about 60°, and a spacing of about 1.75 mm. In some embodiments, distal tip 118 has a smooth exterior surface without any threads thereon. In some embodiments, the distal tip 118 is a solid tip for providing strength during insertion of the implant 100.

Main body 112 further includes a proximal portion 122 extending from the proximal end 116, having hollow bore 124. The majority of hollow bore 124 may be substantially cylindrical. Proximal end of hollow bore 124 may have a particular shape such as a hexagonal perimeter configured to receive an insertion tool therein (not shown). Proximal end of hollow bore 124 may also include detents 125 adapted for receiving and locking a distal end of an insertion tool therein (not shown).

Main body 112 also includes a distal portion 126 extending from the distal end 114, having a substantially rectangular window 128. The window 128 extends from a first lateral side 130 to a second lateral side 132, a top flat interior wall 134, and a bottom flat interior wall 136. At the distal end of the window 128, top wall 134 includes an opening 138a therethrough and bottom wall 136 includes an opening 138b therethrough. Openings 138a, 138b are configured to receive a bolt 700 for mounting wings 300a, 300b, as seen in FIG. 4.

Figure 4:
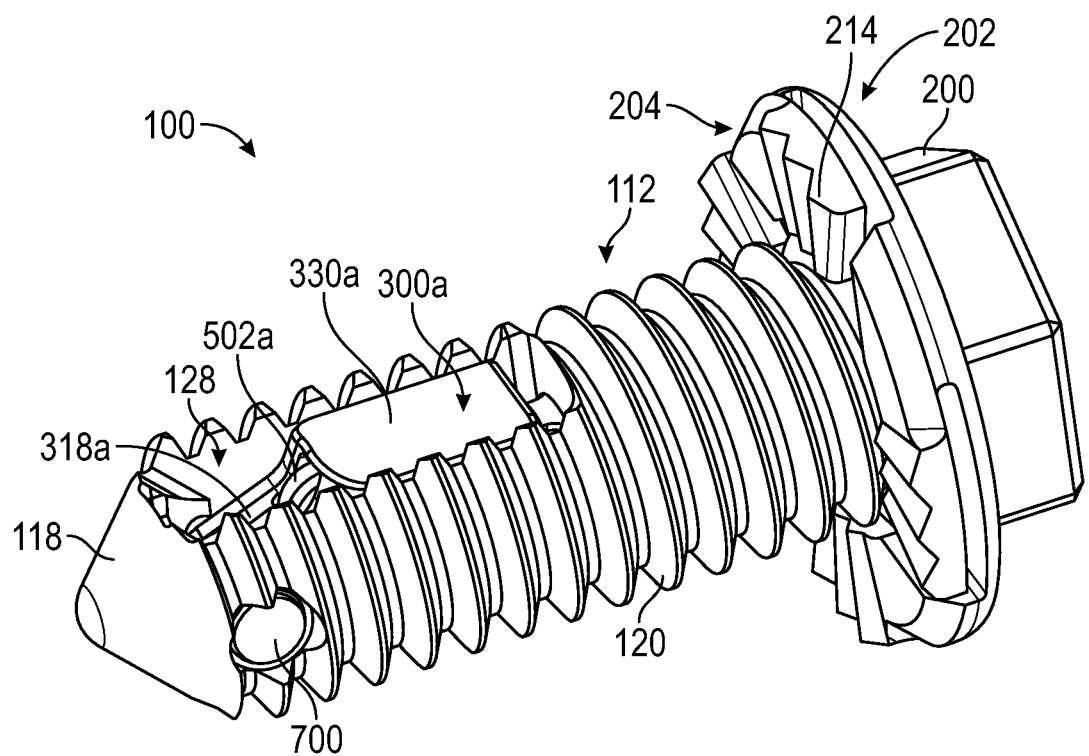
FIG. 4 is a perspective view of the first embodiment of the implant of the invention in the closed configuration.
Figure 15:
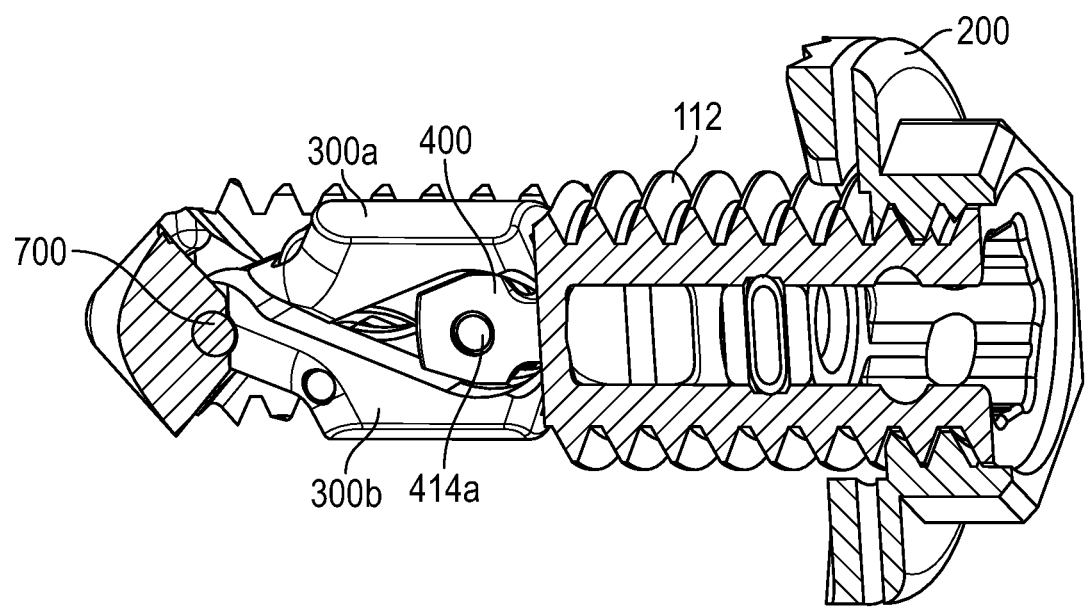
FIG. 15 is another cross-sectional view of the first embodiment of the implant of the invention in the closed configuration.

FIGS. 4 and 15 illustrate implant 100 with wings 300a, 300b in a closed configuration. Window 128 of main body 112 is configured to house a distal portion of the plunger 400, first and second linkages 500a, 500b, and first and second wings 300a, 300b when in the closed configuration.

Figure 2:
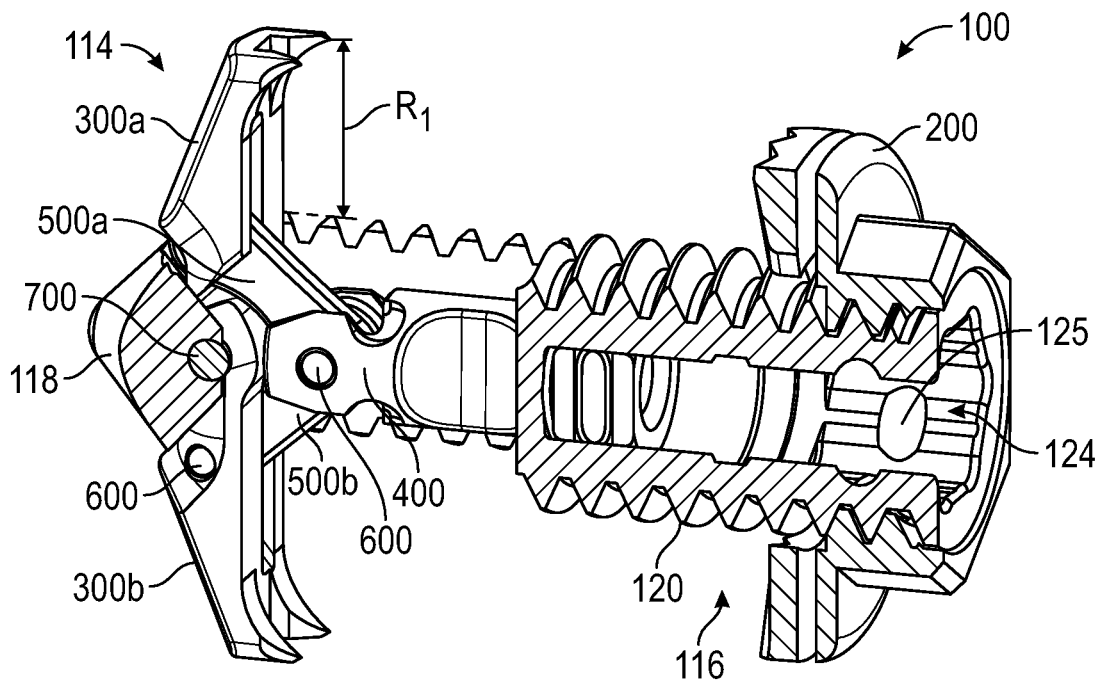
FIG. 2 is a cross-sectional view of the first embodiment of the implant of the invention in an open configuration.
Figure 5:
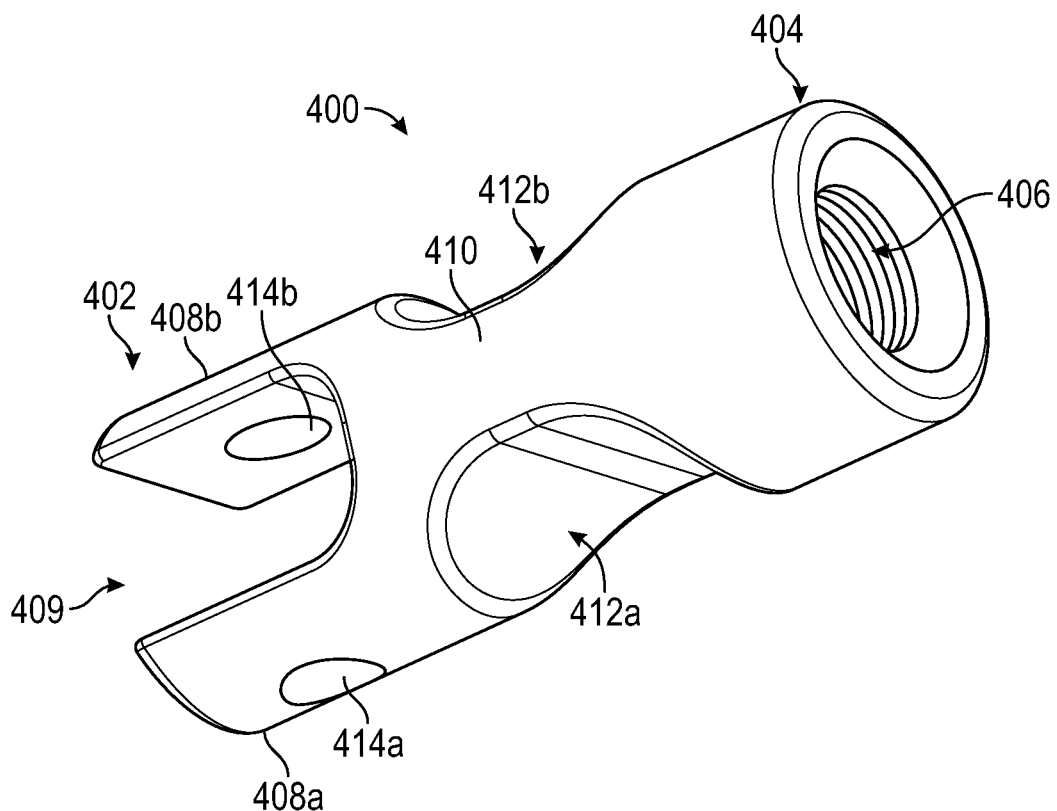
FIG. 5 is a perspective view of an embodiment of a plunger of the invention.

FIG. 5 illustrates an embodiment of plunger 400. Plunger 400 has a distal end 402 and proximal end 404. Proximal end 404 is configured to be located within the bore 124 of main body 112 and distal end 402 is configured to be located within the window 128 of the main body 112, as seen in FIG. 2. Plunger 400 can be moved longitudinally within the bore 124 and window 128 to open and close the wings 300a, 300b, as will be described further below.

With respect to FIG. 5, proximal end of plunger 400 has a central bore 406 for receiving an inserter device (not shown) therein. In some embodiments, central bore 406 of plunger 400 may be threaded to cooperate with threading on an inserter device. Plunger 400 has a substantially Y-shaped construction, having a first arm 408a and a second arm 408b extending from a solid central portion 410. First arm 408a and second arm 408b have a space 409 therebetween. Central portion 410 has two opposed curved indentations 412a, 412b on an outer side, as can be seen in FIG. 5. First arm 408a and second arm 408b each have a hole 414a, 414b extending therethrough for receiving a mounting pin 600 therein. In order to connect wings 300a, 300b to the plunger 400, linkages 500a, 500b are mounted within the space 409 between the arms 408a, 408b.

In an alternative embodiment, a plunger may have two heads having a T-shape or dove-tail feature that rides in a mating grove on the underside of wings 300a, 300b. In a further alternative embodiment, a plunger may be connected by an umbrella-like feature having linkages that ride within a groove on an underside of the wings 300a, 300b.

Figure 6A:
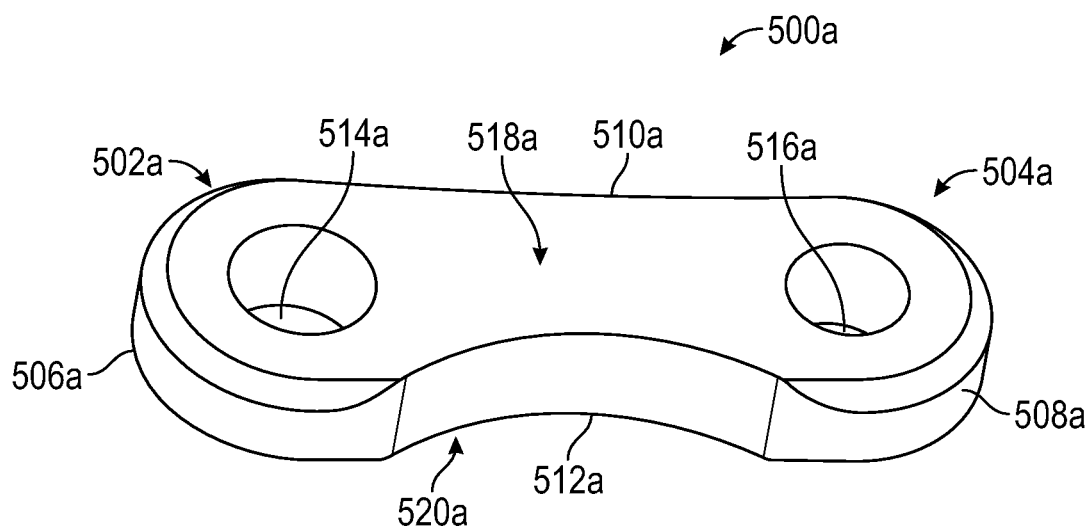
FIG. 6A is a perspective view of an embodiment of a first linkage of the invention.
Figure 6B:
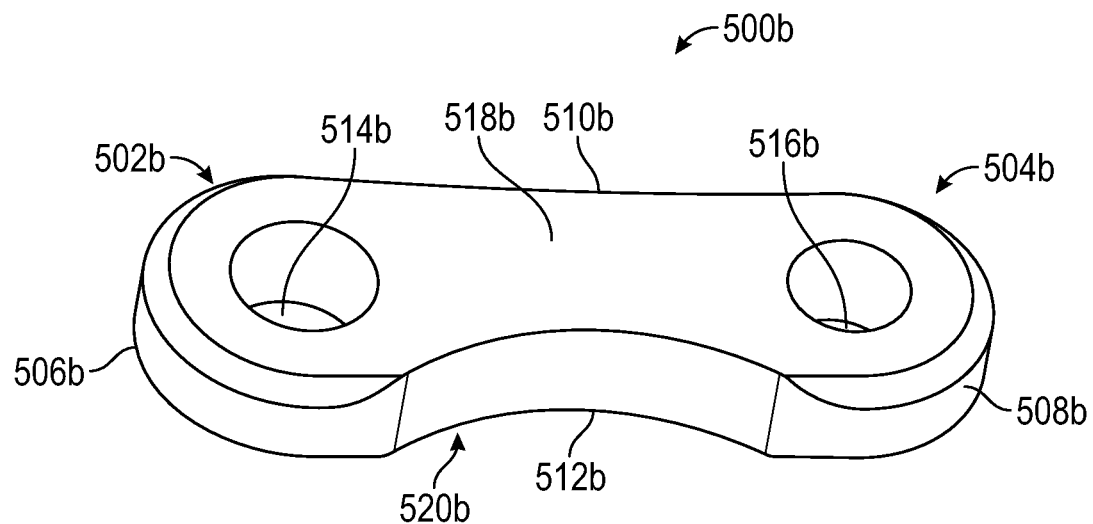
FIG. 6B is a perspective view of an embodiment of a second linkage of the invention.

FIGS. 6A and 6B illustrate an embodiment of first and second linkages 500a, 500b, respectively. First linkage 500a has a first end 502a and a second end 504a. In some embodiments, first linkage 500a is substantially oval shaped with first end 502a having a rounded edge 506a, and second end 504a having a rounded edge 508a. First linkage 500a further includes a straight top edge 510a and an indented curved bottom edge 512a. First end 502a includes a hole 514a extending therethrough and second end 504a includes a hole 516a extending therethrough. Holes 514a and 516a are each configured to receive a mounting pin 600 therein. First linkage 500a includes a substantially planar top surface 518a and a substantially planar bottom surface 520a.

As can be seen in FIG. 6B, second linkage 500b is substantially identical to first linkage 500a. Second linkage 500b has a first end 502b and a second end 504b. In some embodiments, second linkage 500b is substantially oval shaped with first end 502b having a rounded edge 506b, and second end 504b having a rounded edge 508b. Second linkage 500b further includes a straight top edge 510b and an indented curved bottom edge 512b. First end 502b includes a hole 514b extending therethrough and second end 504b includes a hole 516b extending therethrough. Holes 514b and 516b are each configured to receive a mounting pin 600 therein. Second linkage 500b includes a substantially planar top surface 518b and a substantially planar bottom surface 520b.

Figure 7:
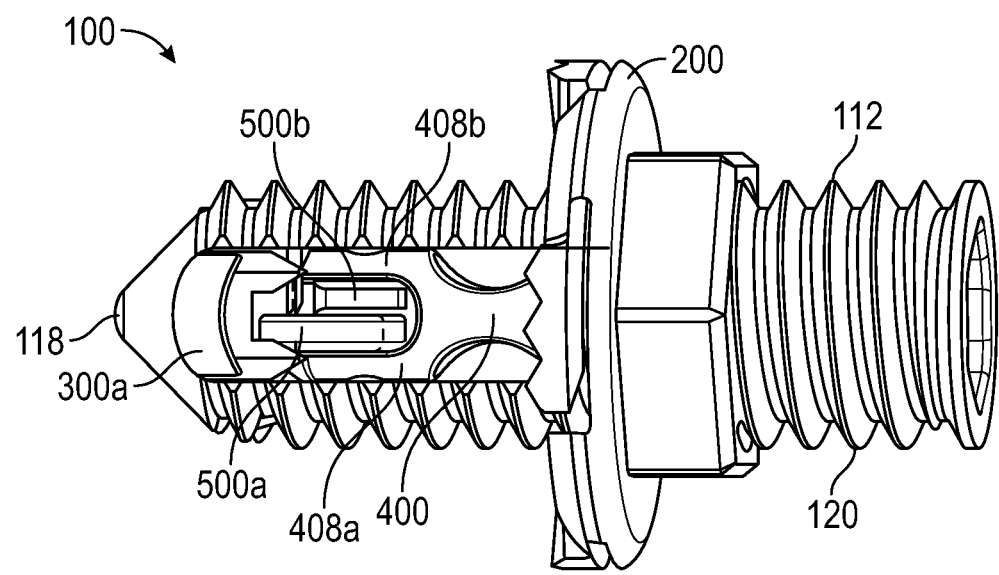
FIG. 7 is another perspective view of the first embodiment of the implant of the invention in an open configuration.

FIG. 7 shows a perspective view of implant 100 in an open configuration, with wing 300a shown in front. As can be seen in FIG. 7, first linkage 500a and second linkage 500b are mounted within the space 409 between arms 408a, 408b of plunger 400.

Figure 8:
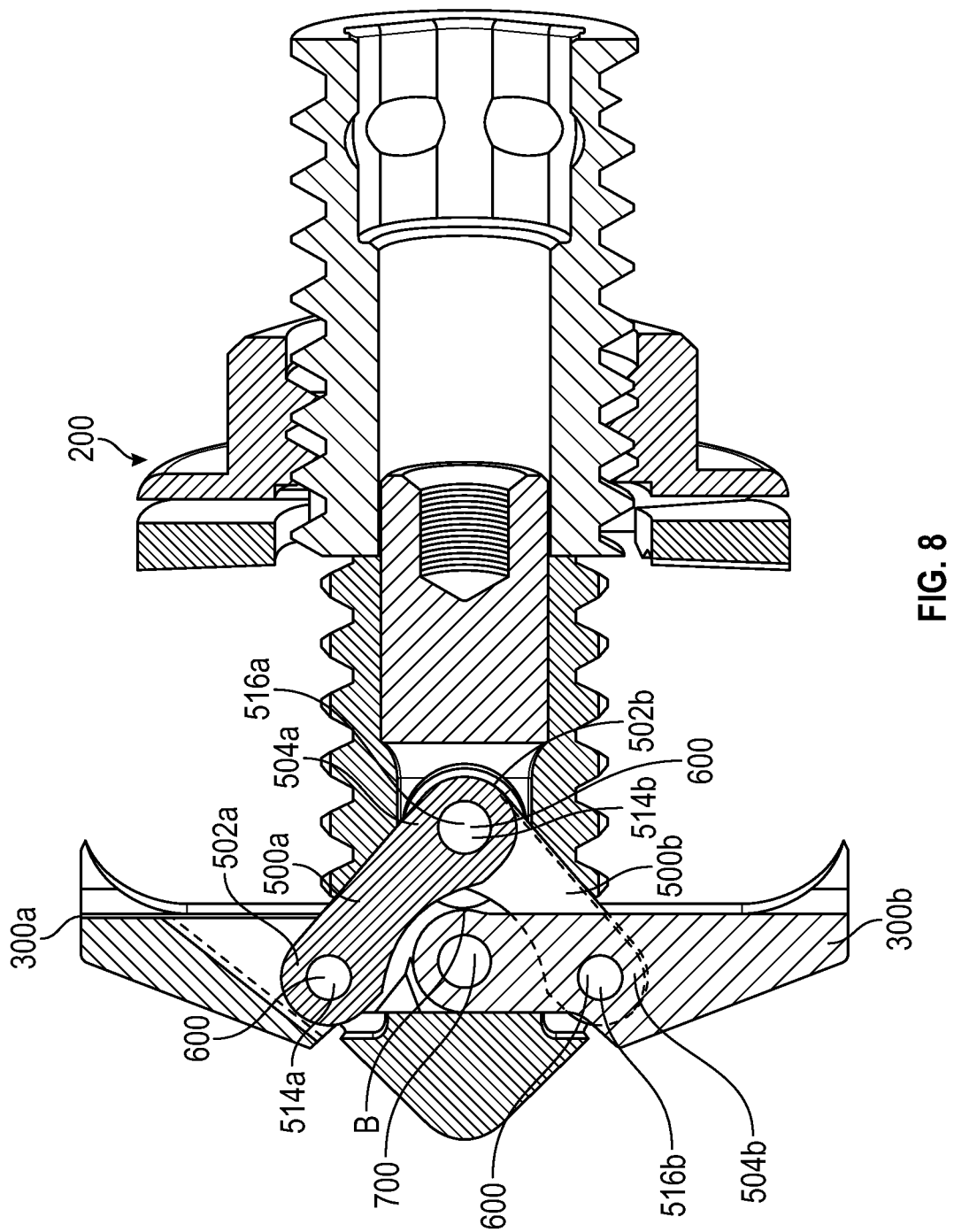
FIG. 8 is a cross-sectional view of the first embodiment of the implant of the invention in the open configuration.

FIG. 8 illustrates a cross-sectional view of implant 100 in an open configuration. As can be seen in FIG. 8, second end 504a of first linkage 500a is connected to first end 502b of second linkage 500b. Planar bottom surface 520a of first linkage 500a is placed in contact with planar top surface 518b of second linkage 500b. As can be seen in FIGS. 2 and 8, a mounting pin 600 is inserted through hole 516a in second end 504a of first linkage 500a, hole 514b in first end 502b of second linkage 500b, hole 414a in first arm 408a of plunger 400, and hole 414b in second arm 408b of plunger 400 to allow for rotation of the linkages 500a, 500b thereabout. The opposite ends of linkages 500a, 500b are connected to the wings 300a, 300b to allow for rotation thereof, as will be described further below.

Figure 9A:
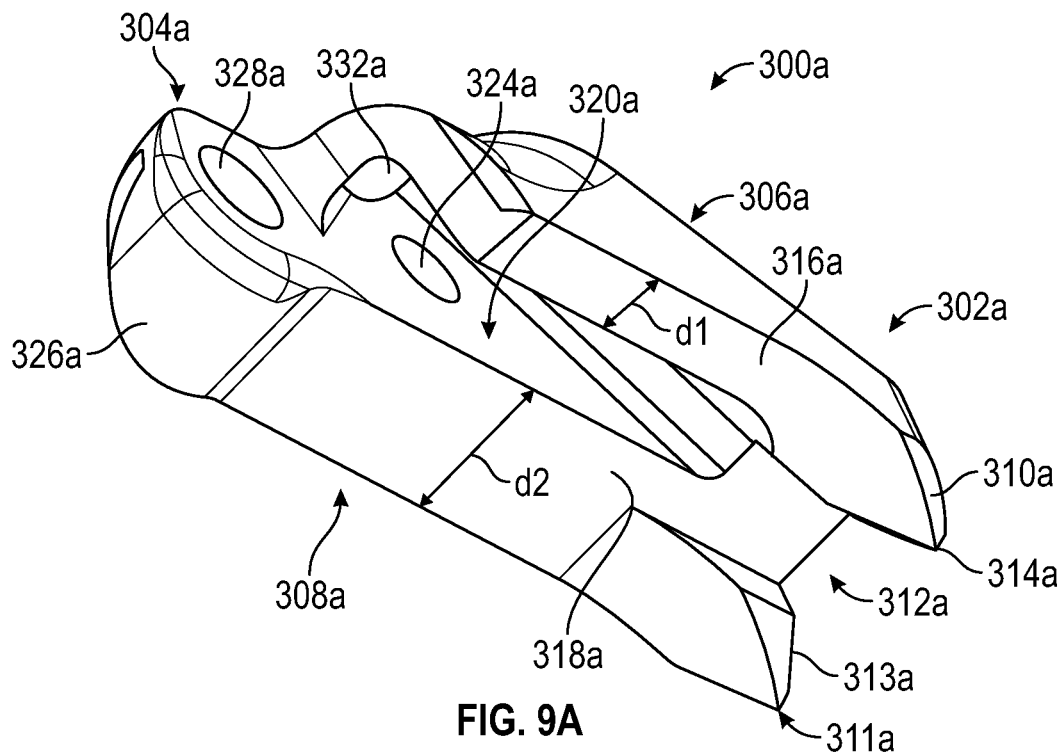
FIG. 9A is a side perspective view of a first embodiment of a first wing of the invention.
Figure 9B:
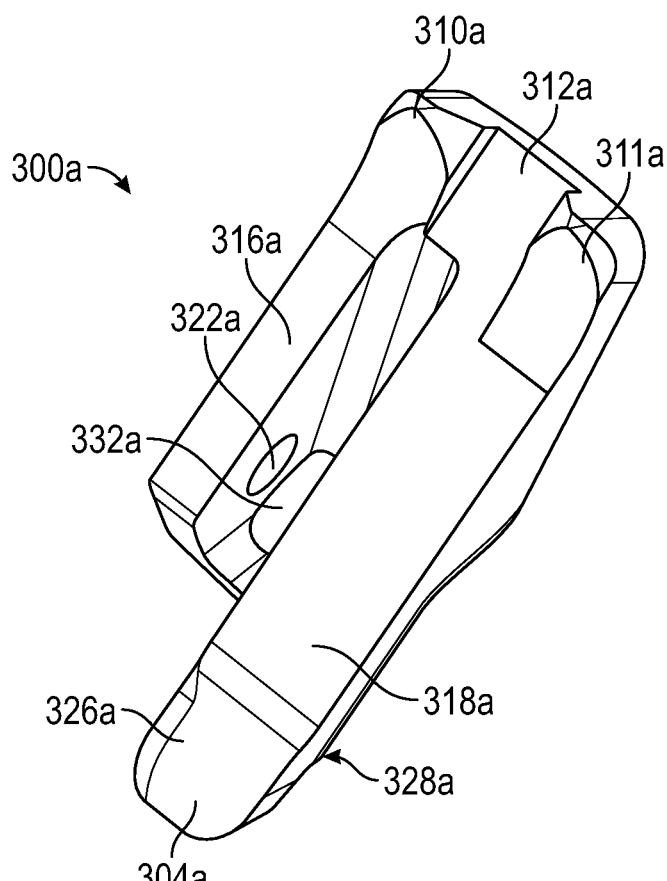
FIG. 9B is a bottom perspective view of the first embodiment of the first wing of the invention.
Figure 9C:
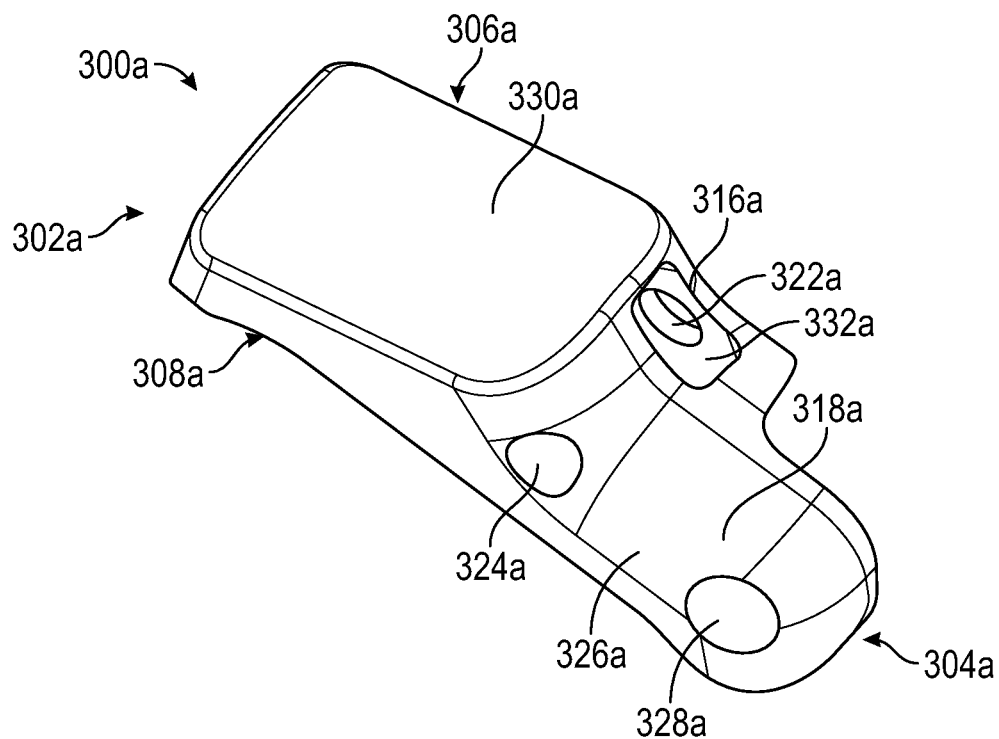
FIG. 9C is a top view of the first embodiment of the first wing of the invention.

FIGS. 9A, 9B, and 9C show perspective views of an embodiment of first wing 300a. Wing 300a has a distal end 302a, a proximal end 304a, a first lateral side 306a, and a second lateral side 308a. In some embodiments, distal end 302a includes at least one fang extending therefrom adapted for engaging bone and/or tissue. In other embodiments, a bottom surface of wing 300a may include a flat roughened surface to achieve gripping of the bone and/or tissue.

In some embodiments, distal end 302a includes first and second fangs 310a, 311a having a gap 312a therebetween. In some embodiments, the dimension of the gap 312a may be about 1.5 mm to about 6 mm. In some embodiments, the gap 312a may be about 3 mm. In some embodiments, first fang 310a has a sharp pointed tip 314a and second fang 311a has a sharp pointed tip 313a. First fang 310a is provided on first lateral side 306a and is connected to first extension 316a. Second fang 311a is provided on second lateral side 308a and is connected to second extension 318a. First extension 316a has a width of d1 and second extension 318a has a width of d2. In some embodiments, width d2 is greater than width d1. In some embodiments, width d1 ranges from about 1.0 mm to about 4.0 mm. In some embodiments, width d2 ranges from about 1.5 mm to about 6.0 mm. A substantially rectangular slot 320a is provided between first extension 316a and second extension 318a for receiving first end 502a of first linkage 500a therein, as can be seen in FIGS. 1, 2 and 7. First extension 316a includes a hole 322a in an inner wall thereof for receiving a pin 600 therein. In some embodiments, hole 322a does not extend fully through the wall of first extension 316a. Second extension 318a includes hole 324a extending therethrough, which is located opposite hole 322a of first extension 316a. A mounting pin 600 is inserted into hole 322a of first extension 316a, hole 514a of first linkage 500a, and hole 324a of second extension 318a to allow for rotation of the wing 300a thereabout.

Wing 300a includes a substantially planar top surface 330a, as can be seen in FIG. 9C. Wing 300a includes a substantially rectangular opening 332a adjacent to top surface 330a. Rectangular opening 332a is adapted to receive first end 502a of first linkage 500a therein in the closed configuration of the wing 300a. Proximal end 304a of wing 300a further includes proximal connector portion 326a having an additional hole 328a for operatively connecting wing 300a to main body 112. Hole 328a is configured to receive a bolt 700 therein.

Figure 10A:
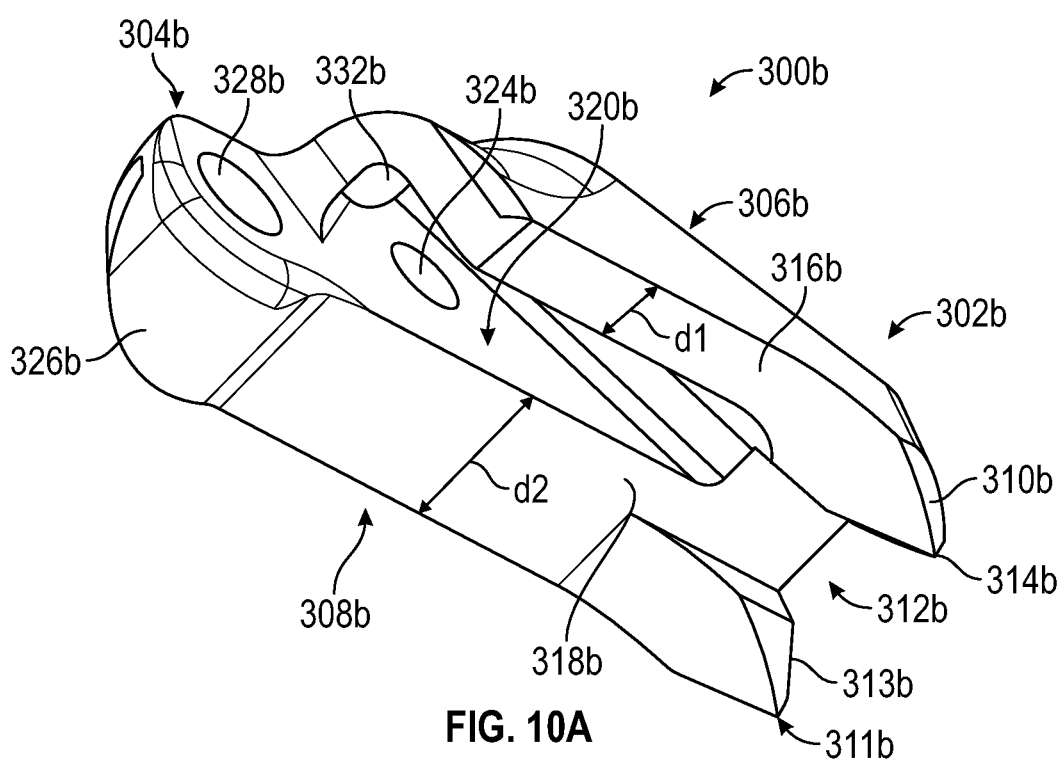
FIG. 10A is a side perspective view of a first embodiment of a second wing of the invention.
Figure 10B:
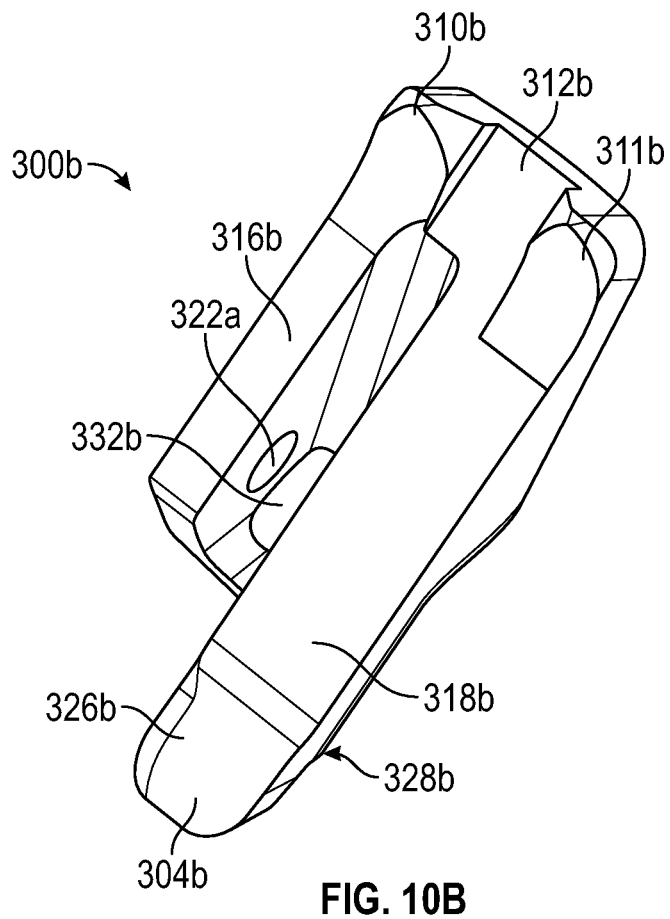
FIG. 10B is a bottom perspective view of the first embodiment of the second wing of the invention.
Figure 10C:
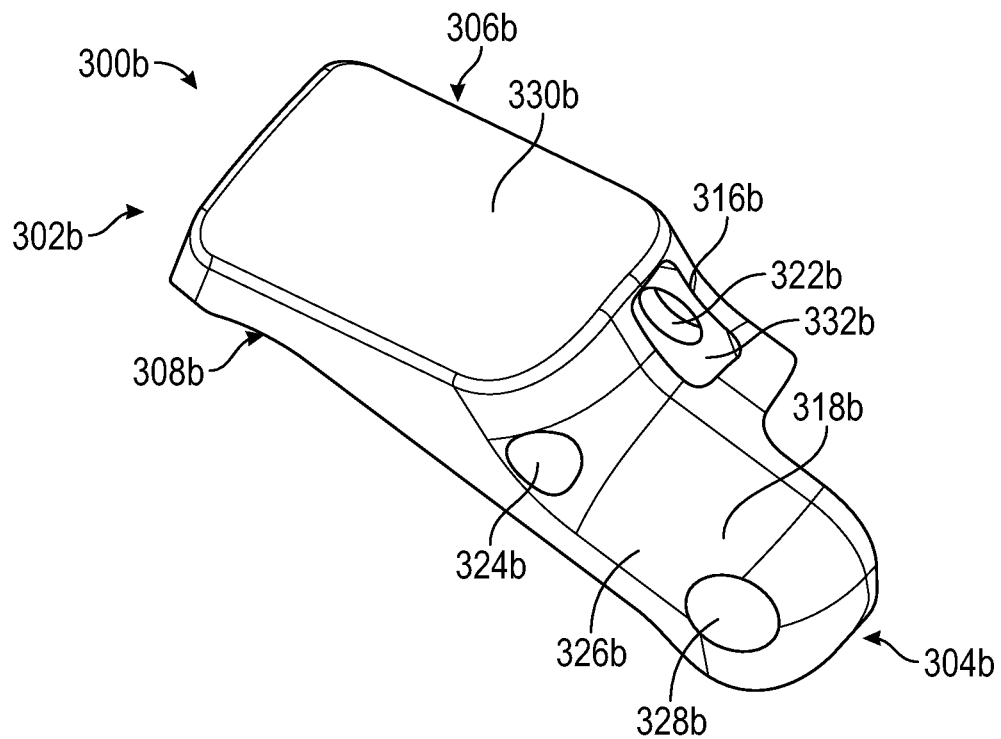
FIG. 10C is a top view of the first embodiment of the second wing of the invention.

FIGS. 10A, 10B, and 10C show perspective views of an embodiment of second wing 300b. Second wing 300b is substantially identical to first wing 300a. Wing 300b has a distal end 302b, a proximal end 304b, a first lateral side 306b, and a second lateral side 308b. In some embodiments, distal end 302b includes at least one fang adapted for engaging bone and/or tissue. In other embodiments, a bottom surface of wing 300b may include a flat roughened surface to achieve gripping of the bone and/or tissue.

In some embodiments, distal end 302b includes first and second fangs 310b, 311b having a gap 312b therebetween. In some embodiments, the dimension of the gap 312b may be about 1.5 mm to about 6 mm. In some embodiments, the gap 312b may be about 3 mm. In some embodiments, first fang 310b has a sharp pointed tip 314b and second fang 311b has a sharp pointed tip 313b. First fang 310b is provided on first lateral side 306b and is connected to first extension 316b. Second fang 311b is provided on second lateral side 308b and is connected to second extension 318b. First extension 316b has a width of d1 and second extension 318b has a width of d2. In some embodiments, width d2 is greater than width d1. A substantially rectangular slot 320b is provided between first extension 316b and second extension 318b for receiving second end 504b of second linkage 500b therein, as can be seen in FIG. 2. First extension 316b includes a hole 322b in an inner wall thereof for receiving a pin 600 therein. Second extension 318b includes hole 324b extending therethrough, which is located opposite hole 322b of first extension 316b. A mounting pin 600 is inserted through hole 322b of first extension 316b, hole 516b of second linkage 500b, and hole 324b of second extension 318b to allow for rotation of the wing 300b thereabout, as can be seen in FIG. 2.

Wing 300b includes a substantially planar top surface 330b, as can be seen in FIG. 10C. Wing 300b includes a substantially rectangular opening 332b adjacent to top surface 330b. Rectangular opening 332b is adapted to receive second end 504b of second linkage 500b therein in the closed configuration of the wing 300b. Proximal end 304b of wing 300b further includes proximal connector portion 326b having an additional hole 328b for operatively connecting wing 300b to main body 112. Hole 328b is configured to receive a bolt 700 therein.

In some embodiments, in the open position, wings 300a, 300b extend circumferentially a distance of about 2 mm to about 15 mm from the main body 112, which may be referred to as the reach, $R_1$, of the wings 300a, 300b. In some embodiments, the spacing of the gap 312a between fangs 310a, 311a may be the same as the spacing of the gap 312b between fangs 310b, 311b. In other embodiments, the spacing of the gap 312a between fangs 310a, 311a may be different from the spacing of the gap 312b between fangs 310b, 311b. The fangs 310a, 311a, 310b, 311b are optimally placed to minimize stress on the spinous process and prevent fracture thereof. The length of any of fangs 310a, 311a, 310b, 311b may be about 0.5 mm to about 5 mm. In some embodiments, each fang can have a different length as desired.

The design of wings 300a, 300b is such that the outer surface acts as a stop relative to main body 112 to control the minimum and maximum movement, thereby preventing closing in on themselves inside the main body 112 and also preventing over-deployment.

Figure 11:
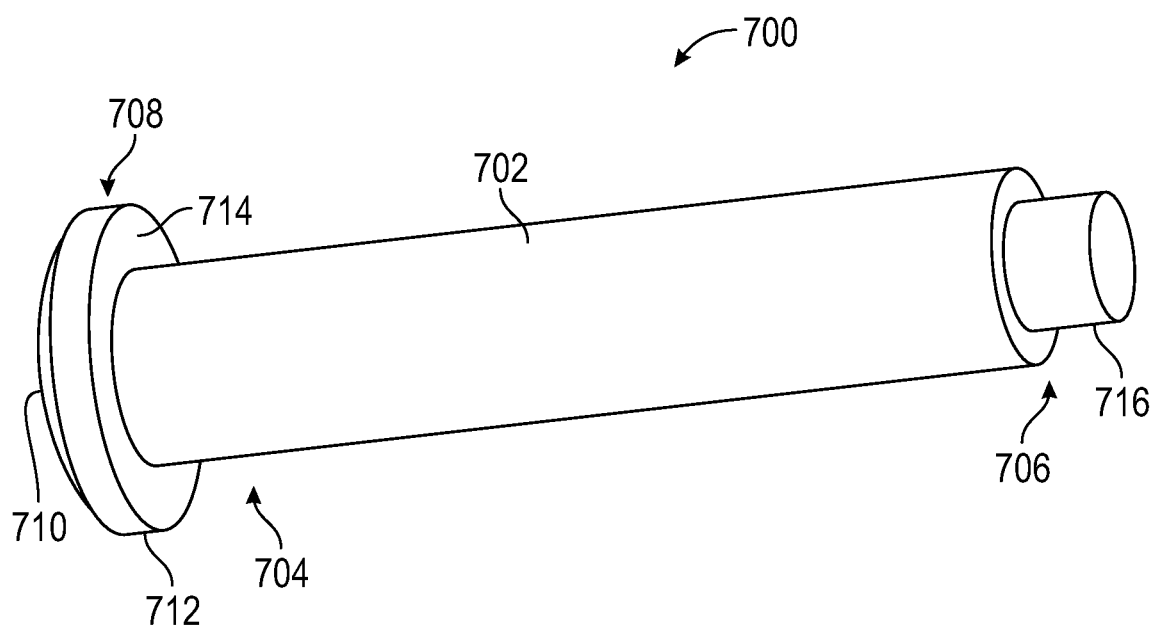
FIG. 11 is a perspective view of a bolt of the invention.
Figure 12:
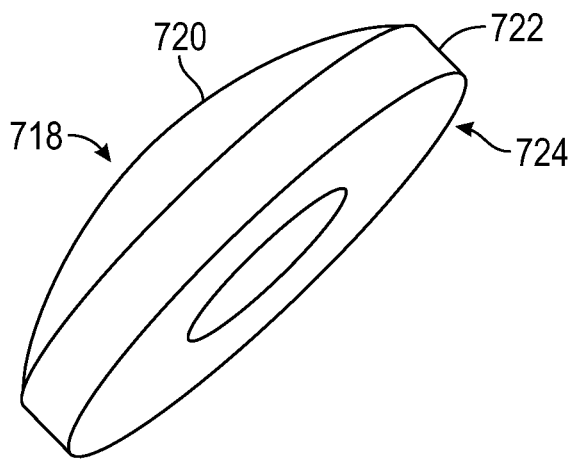
FIG. 12 is a perspective view of a removable head for the bolt of the invention.

FIG. 11 illustrates an embodiment of bolt 700 and FIG. 12 illustrates an embodiment of removable head 718 for connection to bolt 700. Bolt 700 includes a shaft 702 having a proximal end 704 and a distal end 706. Proximal end 704 includes a unitary head 708 having a rounded distal end 710, a side circumferential edge 712, and a flat bottom surface 714. Distal end 706 includes a reduced diameter cylindrical portion 716. Shaft 702 can be inserted through hole 328a of wing 300a, hole 328b of wing 300b, and through openings 138a, 138b of main body 112. Proximal connector portion 326a of wing 300a is thereby adjacent to and connected to proximal connector portion 326b of wing 300b by bolt 700. Shaft 702 has a diameter configured to fit through holes 328a, 328b and to allow the wings 300a, 300b to freely rotate thereabout. Once bolt 700 is inserted through main body 112 and wings 300a, 300b, a removable head 718 may be connected to cylindrical portion 716 to hold the bolt 700 securely in place. The head 718 may be connected by any mechanical fastening means. As shown in FIG. 12, an embodiment of removable head 718 is shaped similarly to unitary head 708, having a rounded distal end 720, a side circumferential edge 722, and a flat bottom surface 724. Head 718 and head 708 are set within the openings 138a, 138b such that the distal ends 710, 720 are recessed and do not extend circumferentially beyond the helical threads 120, as seen in FIG. 4.

Figure 13:
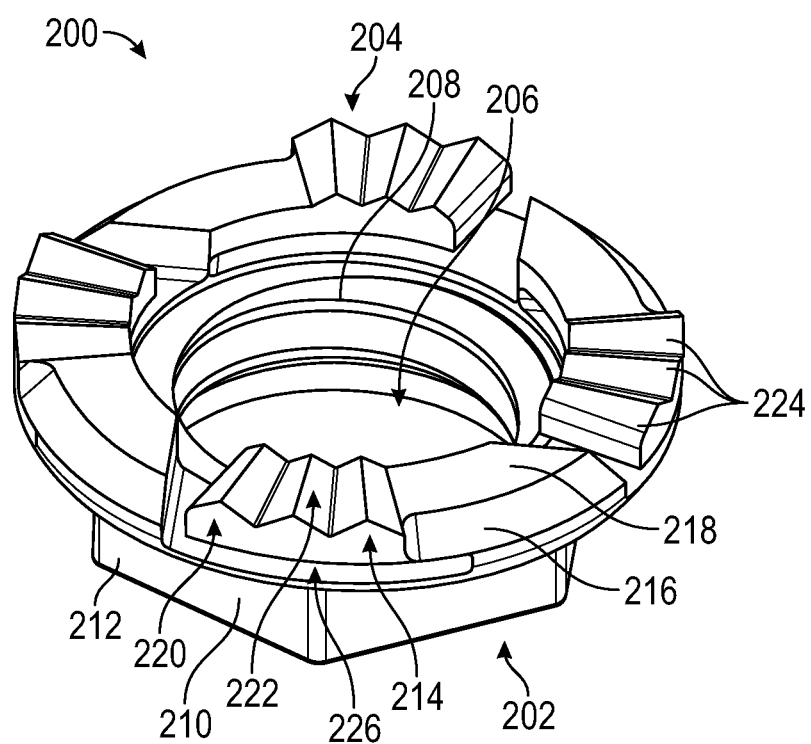
FIG. 13 is a perspective view of an embodiment of a nut of the invention.

FIG. 13 illustrates an embodiment of nut 200. Nut 200 can be provided on the proximal end 116 of main body 112. Nut 200 has a proximal side 202, a distal side 204, and an internal bore 206 therethrough. In some embodiments, internal bore 206 has interior helical threads 208 for cooperating with helical threads 120 on the exterior surface of main body 112. In operation, the nut 200 can be rotated to move the nut longitudinally along the shaft of main body 112 such that the distal side 204 engages tissue and/or bone. In some embodiments, proximal side 202 has a hexagonal extension 210 with flat sides 212. In some embodiments, distal side 204 forms a grip plate having a plurality of flex arms 214. In one embodiment, the grip plate includes four flex arms 214. In other embodiments, the grip plate may include two flex arms, three flex arms, or five or more flex arms.

In some embodiments, each flex arm 214 may have a fixed portion 216 with a smooth top surface 218 and a movable portion 220 with a textured top surface 222. The movable portion 220 may have a space 226 therebelow. The textured top surface 222 is configured to engage bone or tissue when the implant is placed in the body to help anchor the implant 100 in place. The movable portion 220 is configured to flex into open space 226 when the implant 100 is engaged with tissue and/or bone. In some embodiments, the movable portion 220 may flex proximally an amount of from about 1 degree to about 50 degrees. In some embodiments, the movable portion 220 may flex proximally an amount of from about 1 degree to about 10 degrees. In some embodiments, the textured top surface 222 may include teeth, spikes, or any other type of mechanical gripping surface. In one embodiment, the textured top surface 222 may include three substantially triangular shaped teeth 224. In other embodiments, the distal side 204 has a unitary circumferential roughened or textured surface without any flex arms. The nut 200 extends circumferentially a distance of about 2 mm to about 15 mm from the main body 112. In some embodiments, the nut 200 extends circumferentially a distance of about 2 mm to about 8 mm. This reach allows for sufficient bone fixation while ensuring that the implant 100 can be easily inserted through a standard tissue dilation sleeve/tube.

The implant 100 may be provided in different selected sizes to properly fit into the desired space of a particular patient. The implant body diameter may provide for a range of about 6-20 mm spinous process space distraction. In some embodiments, the diameter of the main body 112 may be about 8 mm, about 10 mm, about 12 mm, about 14 mm, or about 16 mm. The sizes of the implant may be color-coded to allow the surgeon to easily identify the size of the implant and match the implant with a properly sized insertion tool (not shown), which may have similar size color-coding.

In some embodiments, all or part of the implant may be composed of titanium or a titanium alloy. In other embodiments, all or part of the implant may be composed of stainless steel. In some embodiments, all or part of the implant may be composed of a polymer or a bioabsorbable material. In some embodiments, the implant may be manufactured by an additive manufacturing process. In some embodiments, the implant may be manufactured by machining or molding. In some embodiments, all or part of the implant may include a coating on at least one surface thereof. In some embodiments, at least one outer surface of the implant may be coated with hydroxyapatite (HA).

In some embodiments, the implant may have a total length of about 30 mm to 45 mm. In some embodiments, the implant may have a total length of about 32 mm to about 34 mm. In some embodiments, the implant may have a total length of about 33 mm.

In some embodiments, main body 112 may be adapted to contain bone graft material therein. The bone graft material may be added to the implant 100 by holding wing 300a open and holding wing 300b closed and injecting bone graft material into the main body 112 (or vice versa). Bone graft material may also be applied around the exterior helical threads 120 before insertion of the implant 100 into the body. In some embodiments, the bone graft material may be viscous to avoid any interference with the proper functioning of the wings 300a, 300b. The volume of the bone graft material may range from about 0.5 cc to about 3.0 cc, or from about 1.2 cc to about 2.5 cc, depending on the size of the implant 100.

Figure 14:
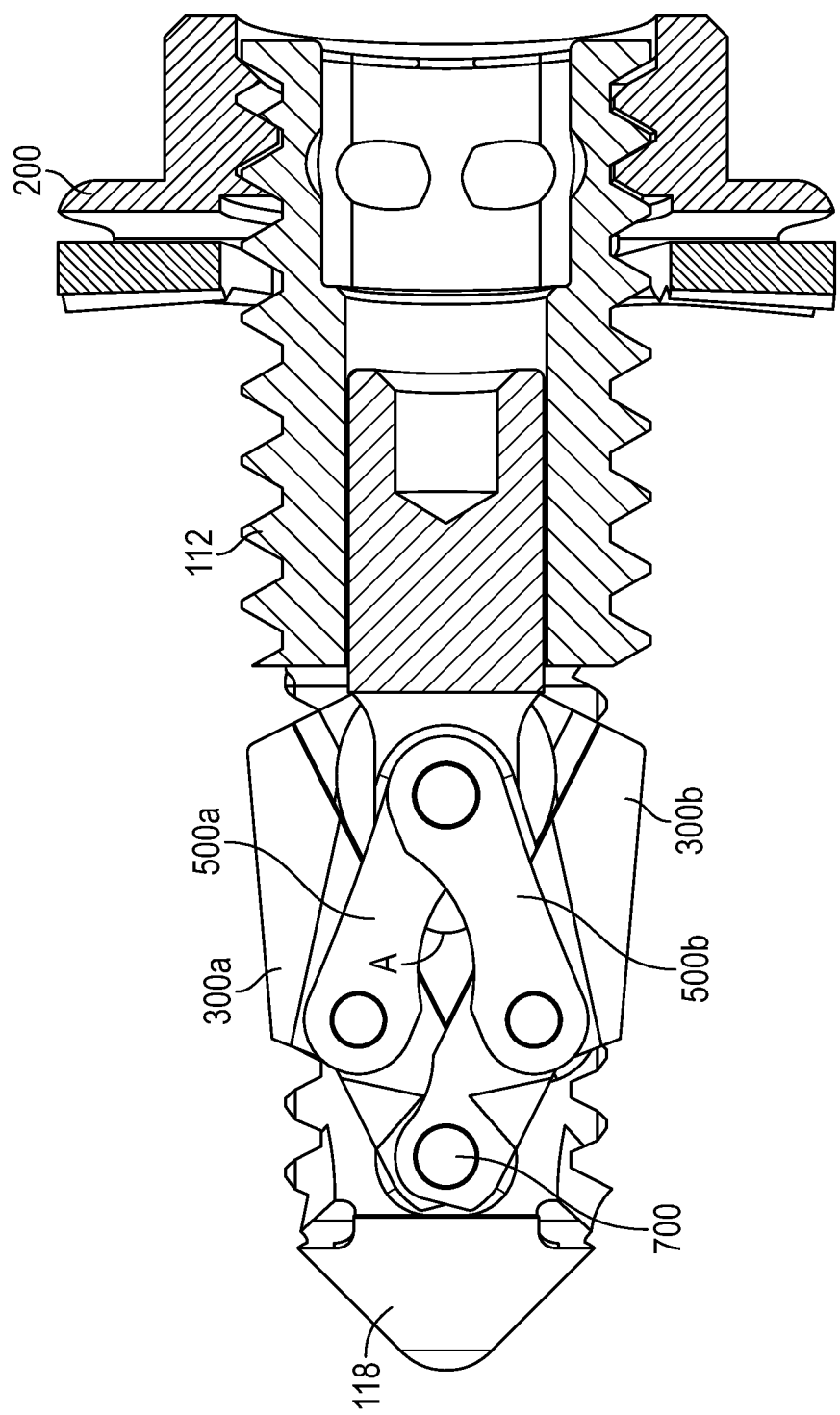
FIG. 14 is a cross-sectional view of the first embodiment of the implant of the invention in the closed configuration.

The implant 100 may be inserted using an inserter device (not shown) into the body of a patient in the closed configuration, as shown in FIGS. 4, 14 and 15. With respect to FIGS. 14 and 15, the plunger 400 is in a proximal position, such that the first and second linkages 500a, 500b form a first angle A therebetween and the wings 300a, 300b are in a closed configuration. Once the implant 100 is inserted into the desired location in the patient's body, the wings 300a, 300b can be moved to an open configuration, as shown in FIGS. 1, 2, 7 and 8. The plunger 400 may be moved distally such that the ends 502a, 504b of the linkages 500a, 500b, respectively, are caused to separate forming a second angle B therebetween, shown in FIG. 8. Angle B is greater than angle A. In some embodiments, angle A is about 35° and angle B is about 85°. As the linkages 500a, 500b separate, the wings 300a, 300b rotate around pins 600 and bolt 700 into an open configuration.

Figure 16:
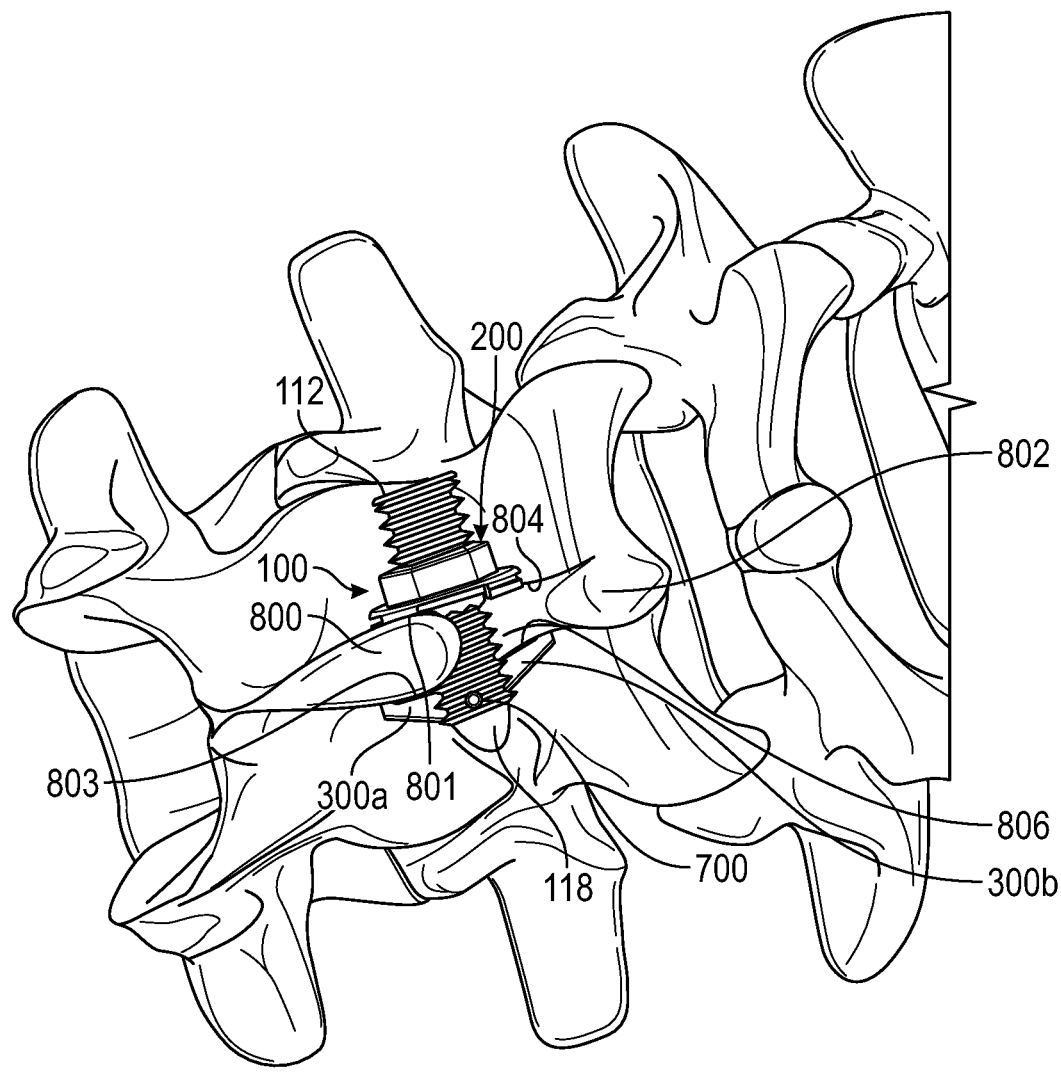
FIG. 16 is a view of the first embodiment of the implant of the invention implanted in the spine of a patient.

The implant may then be moved proximally to engage the wings 300a, 300b with the bone and/or tissue at the implant site, as can be seen in FIG. 16. The nut 200 may then be moved proximally, such as by rotation, to engage the bone and/or tissue as well forming a proximal anchor. Specifically, nut 200 engages a first lateral surface 801 of a first spinous process 800 and a second lateral surface 804 of a second spinous process 802. In some embodiments, the flex arms 214 may be flexed proximally when the nut 200 is tightly engaged with bone and/or tissue at the implant site. Additionally, wings 300a, 300b engage a third opposite surface 803 of first spinous process 800 and a fourth opposite surface 806 of second spinous process 802. Specifically, the fangs 310a, 311a, 310b, 311b of wings 300a, 300b may engage with the bone and/or tissue at the implant site forming a distal anchor. In some embodiments, the wings 300a, 300b and the nut 200 can be engaged on opposite sides of the spinal process when the implant 100 is in place, as seen in FIG. 16.

Features described above as well as those claimed below may be combined in various ways without departing from the scope hereof. The following examples illustrate some possible, non-limiting combinations:

(A1) A spinal implant comprising: a main body, a proximal anchor, a distal anchor, and an internal plunger. The main body has an outer surface, a central bore therein, a proximal end, a distal end, and a longitudinal axis extending therebetween. The proximal anchor comprises a nut having a proximal side, a distal side, and an internal bore. The distal anchor comprises a plurality of wings having a first closed configuration and a second open configuration, wherein the plurality of wings comprises a first wing and a second wing. The internal plunger has a proximal end, a distal end, and is housed within the central bore of the main body. The distal end of the internal plunger is operatively connected to the first wing and the second wing to selectively move the plurality of wings between the first closed configuration and the second open configuration.

(A2) For the spinal implant denoted as (A1), further comprising: a first linkage connecting the first wing to the internal plunger, wherein the first linkage has a proximal end and a distal end; and a second linkage connecting the second wing to the internal plunger, wherein the second linkage has a proximal end and a distal end.

(A3) For the spinal implant denoted as (A2), the distal end of the internal plunger comprises a first arm, a second arm, and a space between the first arm and the second arm, and the proximal end of the first linkage and the proximal end of the second linkage are mounted in the space between the first arm and the second arm of the internal plunger.

(A4) For the spinal implant denoted as any of (A2) through (A3), the first linkage and the second linkage are rotatably attached to the internal plunger by a mounting pin.

(A5) For the spinal implant denoted as any of (A2) through (A4), the distal end of the first linkage is connected to the first wing, and the distal end of the second linkage is connected to the second wing.

(A6) For the spinal implant denoted as any of (A2) through (A5), the first wing includes a first slot for receiving the first linkage therein, and the second wing includes a second slot for receiving the second linkage therein.

(A7) For the spinal implant denoted as any of (A1) through (A6), a distal end of the first wing includes at least one pointed protrusion adapted to engage tissue or bone.

(A8) For the spinal implant denoted as any of (A1) through (A7), a distal end of the second wing includes at least one pointed protrusion adapted to engage tissue or bone.

(A9) For the spinal implant denoted as any of (A1) through (A8), external threads on at a least a portion of the outer surface of the main body; and internal threads within said internal bore of said nut, wherein the internal threads of the nut are configured to cooperate with the external threads of the main body.

(A10) For the spinal implant denoted as any of (A1) through (A9), the distal side of the nut includes at least one flex arm adapted to engage tissue or bone.

(A11) For the spinal implant denoted as any of (A1) through (A10), the at least one flex arm includes a roughened surface or teeth for adapted to engage tissue or bone.

(A12) For the spinal implant denoted as any of (A1) through (A11), the proximal side of the nut comprises a hexagonal extension.

(B1) A spinal implant comprising a main body, a proximal anchor, a distal anchor, and a linkage assembly. The main body has an outer surface, a central bore therein, a proximal end, a distal end, and a longitudinal axis extending therebetween. The main body includes external threads on at a least a portion of the outer surface. The proximal anchor comprises a nut having a proximal side, a distal side, and an internal bore having internal threads. The distal anchor comprises a first wing and a second wing configured to be selectively opened and closed. The linkage assembly connects the first wing and the second wing to the main body.

(B2) For the spinal implant denoted as (B1), the linkage assembly comprises: an internal plunger mounted within the central bore of the main body, a first linkage, and a second linkage.

(B3) For the spinal implant denoted as (B2), the first linkage has a proximal end and a distal end, and the second linkage has a proximal end and a distal end, and wherein the first linkage connects the first wing to the internal plunger and the second linkage connects the second wing to the internal plunger.

(B4) For the spinal implant denoted as (B2) or (B3), a distal end of the internal plunger comprises a first arm, a second arm, and a space between the first arm and the second arm, wherein the proximal end of the first linkage and the proximal end of the second linkage are mounted in the space between the first arm and the second arm of the internal plunger.

(B5) For the spinal implant denoted as any of (B2) through (B4), the first linkage and the second linkage are rotatably attached to the internal plunger by a mounting pin.

(B6) For the spinal implant denoted as any of (B1) through (B5), the proximal side of the nut comprises a hexagonal extension.

(C1) A method of placing a spinal implant at a treatment site comprising: providing a spinal implant in a first closed configuration, placing the spinal implant in a patient at a desired treatment site; and sliding the internal plunger distally along the longitudinal axis to move the plurality of wings to the second open configuration. The method may further comprise sliding the internal plunger proximally along the longitudinal axis to move the plurality of wings to the first closed configuration to withdraw the spinal implant from the patient. The spinal implant comprises a main body, a proximal anchor, a distal anchor, and an internal plunger. The main body has an outer surface, a central bore therein, a proximal end, a distal end, and a longitudinal axis extending therebetween. The proximal anchor comprises a nut having a proximal side, a distal side, and an internal bore. The distal anchor comprises a plurality of wings having the first closed configuration and a second open configuration, wherein the plurality of wings comprises a first wing and a second wing. The internal plunger has a proximal end and a distal end, said internal plunger housed within the central bore of the main body, said distal end of the internal plunger operatively connected to the first wing and the second wing to selectively move the plurality of wings between the first closed configuration and the second open configuration.

(C2) For the method denoted as (C1), further comprising: sliding the internal plunger proximally along the longitudinal axis to move the plurality of wings towards the first closed configuration to engage the plurality of wings with bone or tissue at the treatment site.

(C3) For the method denoted as (C1) or (C2), further comprising: moving the nut distally along the main body to engage the distal side of the nut with tissue or bone.

(C4) For the method denoted as any of (C1) through (C3), sliding the internal plunger proximally along the longitudinal axis to move the plurality of wings to the first closed configuration to withdraw the spinal implant from the patient.

(C5) For the method denoted as any of (C1) through (C4), the proximal side of the nut further comprises a hexagonal extension.

Although the invention has been described with reference to the embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

1. A spinal implant comprising:
    a main body having an outer surface, a proximal end, a distal end, and a longitudinal axis extending between the proximal end and the distal end, said main body including a central bore therein;
    a proximal anchor comprising: a unitary integral nut having a proximal side, a distal side, and an internal bore, wherein the distal side of the nut includes a grip plate having at least one flex arm adapted to engage tissue or bone, said at least one flex arm having a fixed portion and a movable portion with a space proximal thereto;
    a distal anchor comprising: a plurality of wings having a first closed configuration and a second open configuration, wherein the plurality of wings comprises a first wing and a second wing; and
    an internal plunger having a proximal end and a distal end, said internal plunger housed within the central bore of the main body, said distal end of the internal plunger operatively connected to the first wing and the second wing to selectively move the plurality of wings between the first closed configuration and the second open configuration.

2. The spinal implant of claim 1, further comprising:
    a first linkage connecting the first wing to the internal plunger, wherein the first linkage has a proximal end and a distal end; and
    a second linkage connecting the second wing to the internal plunger, wherein the second linkage has a proximal end and a distal end.

3. The spinal implant of claim 2, wherein the distal end of the internal plunger comprises:
    a first arm, a second arm, and a space between the first arm and the second arm,
    wherein the proximal end of the first linkage and the proximal end of the second linkage are mounted in the space between the first arm and the second arm of the internal plunger.

4. The spinal implant of claim 3, wherein the distal end of the first linkage is connected to the first wing, and the distal end of the second linkage is connected to the second wing.

5. The spinal implant of claim 4, wherein the first wing includes a first slot for receiving the first linkage therein, and the second wing includes a second slot for receiving the second linkage therein.

6. The spinal implant of claim 1, wherein a distal end of the first wing includes at least one pointed protrusion adapted to engage tissue or bone.

7. The spinal implant of claim 1, wherein a distal end of the second wing includes at least one pointed protrusion adapted to engage tissue or bone.

8. The spinal implant of claim 1, further comprising:
    external threads on at a least a portion of the outer surface of the main body; and
    internal threads within said internal bore of said nut, wherein the internal threads of the nut are configured to cooperate with the external threads of the main body.

9. The spinal implant of claim 1, wherein the at least one flex arm includes a roughened surface or teeth adapted to engage tissue or bone.

10. The spinal implant of claim 1, wherein said at least one flex arm comprises four flex arms.

11. A spinal implant comprising:
a main body having an outer surface, a proximal end, a distal end, and a longitudinal axis extending between the proximal end and the distal end, said main body including a central bore therein and external threads on at a least a portion of the outer surface;
a proximal anchor comprising: a nut having a proximal side, a distal side, and an internal bore having internal threads, wherein the nut is a single piece, and wherein the distal side of the nut includes a grip plate having at least one flex arm adapted to engage tissue or bone, said flex arm having a fixed portion and a movable portion with a space proximal thereto;
a distal anchor comprising: a first wing and a second wing configured to be selectively opened and closed; and
a linkage assembly connecting the first wing and the second wing to the main body.

12. The spinal implant of claim 11, wherein the linkage assembly comprises:
an internal plunger mounted within the central bore of the main body; a first linkage; and a second linkage.

13. The spinal implant of claim 12, wherein the first linkage has a proximal end and a distal end, and the second linkage has a proximal end and a distal end, and
wherein the first linkage connects the first wing to the internal plunger and the second linkage connects the second wing to the internal plunger.

14. The spinal implant of claim 13, wherein a distal end of the internal plunger comprises a first arm, a second arm, and a space between the first arm and the second arm,
wherein the proximal end of the first linkage and the proximal end of the second linkage are mounted in the space between the first arm and the second arm of the internal plunger.

15. The spinal implant of claim 11, wherein the at least one flex arm includes a roughened surface or teeth adapted to engage tissue or bone.

16. The spinal implant of claim 11, wherein said at least one flex arm comprises four flex arms.

17. A method of placing a spinal implant at a treatment site comprising:
providing a spinal implant in a first closed configuration, said spinal implant comprising:
a main body having an outer surface, a proximal end, a distal end, and a longitudinal axis extending between the proximal end and the distal end, said main body including a central bore therein;
a proximal anchor comprising: a monolithic nut having a proximal side, a distal side, and an internal bore, wherein the distal side of the nut includes a grip plate having at least one flex arm adapted to engage tissue or bone, said flex arm having a fixed portion and a movable portion with a space proximal thereto;
a distal anchor comprising: a plurality of wings having the first closed configuration and a second open configuration, wherein the plurality of wings comprises a first wing and a second wing; and
an internal plunger having a proximal end and a distal end, said internal plunger housed within the central bore of the main body, said distal end of the internal plunger operatively connected to the first wing and the second wing to selectively move the plurality of wings between the first closed configuration and the second open configuration;
placing the spinal implant in a patient at a desired treatment site; and
sliding the internal plunger distally along the longitudinal axis to move the plurality of wings to the second open configuration.

18. The method of claim 17, further comprising:
sliding the internal plunger proximally along the longitudinal axis to move the plurality of wings towards the first closed configuration to engage the plurality of wings with bone or tissue at the treatment site.

19. The method of claim 17, further comprising:
moving the nut distally along the main body to engage the distal side of the nut with tissue or bone.

20. The method of claim 17, further comprising:
sliding the internal plunger proximally along the longitudinal axis to move the plurality of wings to the first closed configuration to withdraw the spinal implant from the patient.

* * * * *